United States Patent [19]
Pasqualini et al.

[11] Patent Number: 5,496,929
[45] Date of Patent: Mar. 5, 1996

[54] RADIOPHARMACEUTICAL PRODUCT HAVING IN PARTICULAR A CEREBRAL TROPISM COMPRISING A NITRURO COMPLEX OF A TRANSITION METAL AND METHOD FOR PREPARING SAID PRODUCT

[75] Inventors: Roberto Pasqualini, Clamart; Emmanuel Bellande, Saulx les Chartreux; Véronique Comazzi, Issy les Joulineaux; Jacques Lainé, Antony, all of France

[73] Assignee: Cis Bio International, Saclay, France

[21] Appl. No.: 178,244

[22] PCT Filed: Jul. 25, 1994

[86] PCT No.: PCT/FR92/00718

§ 371 Date: May 19, 1994

§ 102(e) Date: May 19, 1994

[87] PCT Pub. No.: WO93/01839

PCT Pub. Date: Apr. 2, 1993

[30] Foreign Application Priority Data

Jul. 22, 1991 [FR] France ................... 91 09231

[51] Int. Cl.[6] .................................. A61K 43/00
[52] U.S. Cl. ................................ 534/10; 534/14
[58] Field of Search .............. 534/14, 10; 424/1.11, 424/1.65

[56] References Cited

U.S. PATENT DOCUMENTS 5,288,476  2/1994  Pasqualini et al. ............... 534/10
5,301,278  4/1994  Pasqualini et al. ............... 534/14

FOREIGN PATENT DOCUMENTS 0279417  8/1988  European Pat. Off. .
8503063  7/1985  WIPO .
9006137  6/1990  WIPO .
9119516  12/1991  WIPO .
9200982  1/1992  WIPO .

*Primary Examiner*—Shean Wu
*Attorney, Agent, or Firm*—Oblon, Spivak, McClelland, Maier & Neustadt

[57] ABSTRACT

The invention concerns a radiopharmaceutical product having in particular a cerebral tropism comprising a nitruro complex of a transition metal and the method for preparing said product. This complex satisfies the formula $(M\equiv N)L^1 L^2$ (I) in which M is a transition metal, such as Tc99m, Re 186 or Re188, and $L^1$ and $L^2$, which may be identical or different, satisfy the formula

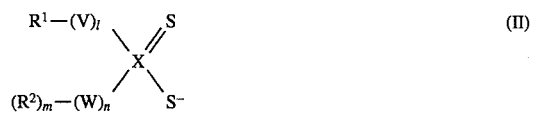

in which $R^1$ and $R^2$ may be alkyl radicals, V and W may be O, S or Se, n=0 or 1, l=0 or 1, m=0 or 1, and X represents N—C, C, or As.

14 Claims, No Drawings

RADIOPHARMACEUTICAL PRODUCT HAVING IN PARTICULAR A CEREBRAL TROPISM COMPRISING A NITRURO COMPLEX OF A TRANSITION METAL AND METHOD FOR PREPARING SAID PRODUCT

FIELD OF THE INVENTION

The present invention concerns a radiopharmaceutical product having in particular a cerebral tropism which includes a nitruro complex of a transition metal comprising a portion M≡N in which M represents the transition metal.

BACKGROUND OF THE INVENTION

It is understood in this document that a transition metal is a metal whose layer d is partially filled with the normal oxidation number of this metal. This concerns elements filling the periods III to XII of the periodic table of elements with eighteen columns.

For example, these metals may be Tc, Ru, Co, Pt, Fe, Os, Ir, W, Re, Cr, Mo, Mn, Ni, Rh, Pd, Nb and Ta.

Technetium nitruro complexes have been described by J. Baldas and al. in the following documents : international patent application WO-85/03 063 and the book entitled "Technetium in Chemistry and Nuclear Medicine" Ed. M. Nicolini, G. Bandoll, U. Mazzi, Cortine Int. Verone, 1986, pages 103 to 108.

In these documents, the preparation of technetium nitruro complexes is described via the substitution reaction on $TcNCl_4$ and it is specified that these complexes may be used as radiopharmaceutical products, but these documents provide no conclusive result concerning the fixation of these complexes in the human body and thus give no indication as to their tropisms in relation to certain organs, especially the brain. Moreover, the ligands tested are mainly diethylenetri-aminepentacetate (DTPA), methylene disphosphonate (MDP), cysteine (CYS), gluconate (GLUC), ethane-1-hydroxy-1,1-disphosphonate (EHDP), N-(2,6-dimethylphenyl-carbamoylmethyl)iminodiacetate (HIDA), N-( 2,6-diisopropylphenylcarbamoylmethly)iminodiacetate (PIPIDA) and dimercaptosuccinate (DMSA).

Radiopharmaceutical products able to be used for the optical image formation of the brain need to possess certain characteristics which first of all are to be able to traverse the hematoencephalic barrier and be fixed and accumulated in the brain within a relatively short period of time at a high concentration and to remain there for a sufficient period so that an examination can be made.

Technetium neutral complexes possessing these characteristics are described in the documents EP-A- 0 394 126, EP-A 163 119, EP-A- 0 279 417, EP-A 0 194 843 and FR-A- 2 651 232.

In the documents EP-A- 194 843, EP-A- 163 119, FR-A 2 651 232 and EP-A- 0 394 126, the complexes used include ligands with amino ceto or thiol groups, which may be coupled to a radioactive metallic ion, such as TcO. These documents do not deal with technetium nitruro complexes.

However, the document EP-A 0 279 417 does refer to diaminodithiols ligands with ester substituents which may be coupled to a pattern Tc≡N so as to form nitruro complexes able to be used for forming an optical image of the brain.

The document WO-90/06137 also describes transition metal nitruro complexes able to be used as a cardiac tropism radiopharmaceutical product, but the biodistribution results obtained with the complexes of the examples of this document show that they are scarcely retained by the brain.

However, following research conducted on other radiopharmaceutical products of the same type, some of them have been found to possess satisfactory properties enabling them to be used as diagnostic or therapy products having a cerebral tropism for, for example, the use of a scintiscanner examining the brain.

SUMMARY OF THE INVENTION

Also, the present invention concerns new radiopharmaceutical products which include a complex of a transition metal satisfying the formula:

$$(M\equiv N)\, L^1\, L^2 \quad\quad (I)$$

in which $L^1$ and $L^2$, which may be identical or different, satisfy the formula:

in which $R^1$ and $R^2$, which may be identical or different, represent a linear or branched alkyl radical with 1 to 10 carbon atoms, possibly substituted by at least one group selected from the groups —O—$R^3$, —OOC$R^3$, —COO$R^3$, V-CONR$^4$R$^5$ or —NR$^4$R$^5$ in which $R^3$ is a linear or branched alkyl radical with 1 to 5 carbon atoms, and $R^4$ and $R^5$, which may be identical or different, are hydrogen atoms or linear or branched alkyl radicals with 1 to 5 carbon atoms, or in which $R^1$ and $R^2$ together form a hydrocarbonated cycle possibly containing one or several heteroatoms, possibly substituted by at least one group selected from —O$R^3$, —COO$R^3$, —OOC$R^3$, V-CONR$^4$ R$^5$ or —NR$^4$R$^5$ in which $R^3$, $R^4$, and $R^5$ are as defined above, V and W may be identical or different and represent O, S or Se, X represents C, N—C, P or As, and l, m and n, which may be identical or different, are equal to 0 or 1, m and n being equal to 0 when X represents C, and m being equal to 1 when X represents N—C, P or As, provided 1) when X represents —N—C—, $R^1$ or $R^2$ is an alkyl radical substituted by at least one —COO$R^3$ and or CONR$^4$R$^5$ group, or $R^1$ and $R^2$ together form a substituted hydrocarbonated cycle possibly containing one or several heteroatoms, and 2) when X represents P, with V and W representing O, $R^1$ or $R^2$ is a substituted alkyl radical or $R^1$ and $R^2$ together form a substituted hydrocarbonated cycle possibly containing one or several heteroatoms.

When $R^1$ and $R^2$ together form with X a hydrocarbonated cycle possibly containing one or several heteroatoms, the number of atoms of this cycle, including the atom of X, is generally from 5 to 7.

In the radiopharmaceutical products of the invention, the transition metal nitruro complex may be of different types.

Thus, according to one first embodiment of the invention, the ligands $L^1$ and $L^2$ are of the dithiocarbamate type and satisfy the formula:

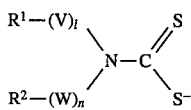  (III)

in which $R^1$ or $R^2$ is an alkyl radical substituted by $V\text{-}CONR^4R^5$, or $-COOR^3$.

Preferably, l and n are equal to 0. Generally speaking, $R^1$ is an alkyl radical substituted by $V\text{-}CONR^4R^5$ or $-COOR^3$, and $R^2$ is an alkyl radical or alkyl radical substituted by $-COOR^3$.

By way of example, $L^1$ and $L^2$ may satisfy the following formulae:

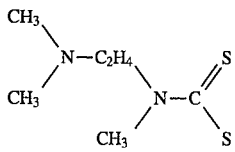  (IV)

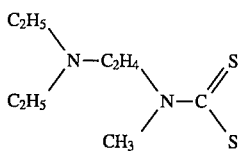  (V)

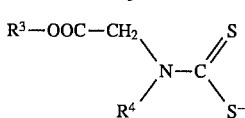  (VI)

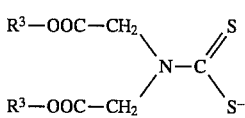  (VIII)

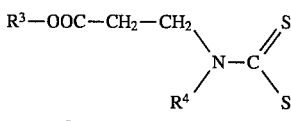  (VIII)

in which $R^3$ is the ethyl or methyl radical and $R^4$ is the methyl, ethyl or propyl radical.

According to a second embodiment of the invention, the ligands $L^1$ and $L^2$ and satisfy the formula:

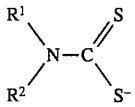  (IX)

in which $R^1$ and $R^2$ together form a hydrocarbonated cycle substituted by a $COOR^3$ group.

The hydrocarbonated cycle formed by

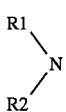

include, for example, 5 to 7 atoms, including the nitrogen atom.

By way of example of such a ligand, it is possible to cite the one satisfying the formula:

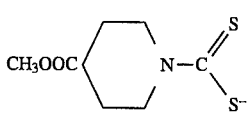  (X)

According to a third embodiment of the invention, the ligands $L^1$ and $L^2$ satisfy the formula:

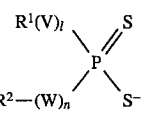  (XI)

in which $R^1$ and $R^2$ are alkyl radicals, possibly substituted.

When l and n are equal to 0, the ligands $L^1$ and $L^2$ are of the dithiophosphinate type.

Dithiophophinate ligands may possibly be those satisfying the following formulae:

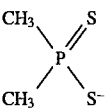  (XII)

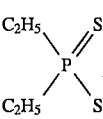  (XIII)

In this third embodiment, $L^1$ and $L^2$ may be identical or different.

In this third embodiment of the invention, when $l=n=1$, the ligands $L^1$ and $L^2$ are of the dithiophosphate type and satisfy the formula:

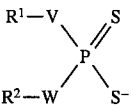  (XIV)

in which V and W are O, S or Se, for example 0, and $R^1$ and $R^2$ have the significance given above.

According to a fourth embodiment of the invention, $L^1$ and $L^2$ are of the dithiocarboxylate type and satisfy the formula:

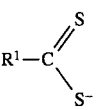  (XV)

In the complexes of the invention, the transition metal used depends in particular on the application of the radiopharmaceutical product.

Thus, when it is desired to use the product for diagnosis, a radioactive transition metal is used, such as technetium $^{99}$m, having a relatively short period.

Where it is desired to use the radiopharmaceutical product for therapy, a transition metal is used emitting an effective radiation for therapy and having a longer period of life, such as rhenium, for example Re-186 or Re-188.

The technetium nitruro complexes used in the invention may be prepared by the Baldas method. However, they are preferably prepared by a simpler method, easy to implement in a hospital department and resulting in obtaining higher yields.

This method includes the following successive stages:

1) making a dissolved oxygenous compound of a transition metal M react with:

a) a first reactive agent selected from the group of aliphatic and aromatic polyphosphines and phosphines, possibly substituted, and b) a second reactive agent selected from ammonium nitrides or pharmaceutically acceptable metals and nitrogenous ligands comprising a pattern >N-N< in which the Ns are linked to hydrogen atoms and/or monovalent organic groups, or in which one of the Ns is linked to the carbon atom of a bivalent organic group by means of a double link, the other N being linked to hydrogen atoms and/or to monovalent organic groups, and 2) making the intermediate product obtained in the first stage react with a compound satisfying the formula:

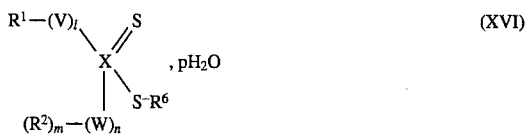 (XVI)

in which $R^1$, $R^2$, V, W, l, m, n and X have the significance given above,
$R^6$ being an alkaline metal ion, $H^+$ or $NH_4^+$, and p is equal to 0 or a whole number ranging from 1 to 5.

When this method is implemented by using technetium as a transition metal, the oxygenous compound of the transition metal may be ammonium or alkaline metal pertechnetate. Where the transition metal is rhenium, it is possible to use an ammonium or alkaline metal perrhenate.

In the first stage of the method, a first technetium nitruro complex is thus prepared which is then made to react with the compound of formula (XII) so as to exchange the first and second reactive agents by means of this compound.

In order to embody the reaction, the first and second reactive agents may be aseptically introduced into a receptacle and then the required quantity of the oxygenous transition metal compound, such as technetium pertechnetate 99m, is added after having adjusted the pH to an appropriate value by adding acid or a base. Then the reaction may be carried out at ambient temperature or at a higher temperature of between 50° and 100° C. The temperature and the pH used depend in particular on the second reactive agent. Generally speaking, this is effected between a pH of 2 and 7.

In the first stage, it is possible to use the first and second reactive agents in the form of aqueous, alcoholic or hydroalcoholic solutions and simply add these solutions to the oxygenous compound of the transition metal.

In the second stage, the product obtained in the first stage is made to react with the compound of formula (XII) in an aqueous solution generally with a pH of more than 7, for example in a sodium carbonate-bicarbonate buffer.

In this second stage, it is possible to use an alcoholic or hydroalcoholic solution of the compound (XII).

The first reactive agent used for obtaining the formation of a nitruro complex is an organic ligand with a donor phosporus atom selected from aliphatic and aromatic polyphosphines, possibly substituted.

The phosphines able to be used may satisfy the formula:

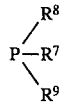

in which $R^7$, $R^8$ and $R^9$, which may be identical or different, represent a hydrogen atom, an alkyl radical, an aryl radical, an alcoxy radical or an alkyl or aryl radical substituted by a group selected from the amino, amido, cyano, sulphonate, chloro, fluoro or carboxylate radicals.

By way of examples of phosphines of this type, these may be triphenylphosphine, trisulphonated triphenylphosphine, diethylphenylphosphine, triethylphosphine, trimethylphosphine and tris(2-cyanoethyl)phosphine $P(CH_2-CH_2CN)_3$.

In the first stage, it is possible to use as a second reactive agent, either an alkaline or ammonium metal nitride, for example sodium nitride, or a nitrogenous ligand comprising the pattern N-N as in hydrazine and its derivatives. It is possible to use a large number of nitrogenous ligands of this type. Generally speaking, as a nitrogenous ligand, it is preferable to use dithiocarbazic acid or one of its derivatives, as described in the document WO-89/00608, or nitrogenous ligands satisfying the formula:

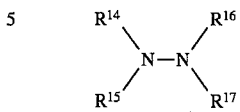

in which $R^{14}$, $R^{15}$ and $R^{16}$, which may be identical or different, represent a hydrogen atom, an alkyl radical, an aryl radical, an alcoxy radical, an alkyl radical substituted by at least one group selected from the hydroxy, carboxy, amino, amido and mercapto radicals or an aryl radical substituted by at least one group selected from halogen atoms and the alcoxy, hydroxy, amino, mercapto radicals and an amino radical substituted by at least one alkyl radical, $R^{17}$ represents a radical satisfying the formulae:

$$-SO_2R^{18} \text{ or } -CO\ R^{19}$$

in which $R^{18}$ is a phenyl group, possibly substituted by at least one substituent selected from the halogen atoms and the alkyl radicals, and $R^{19}$ is a hydrogen atom, $-NH_2$ or a radical selected from the alkyl radicals, the alkyl radicals substituted by at least one group selected from the cyano, pyridyl and $-CO-NH-NH_2$ groups, a phenyl radical, a phenyl radical substituted by at least one substituent selected from $-OH$, $NH_2$ and the alkyl and alcoxy radicals.

In this formula, the alkyl and alcoxy radicals may be linear or branched radicals and preferably with 1 to 4 atoms of carbon, such as a methyl or methoxy radical.

The aryl radicals are radicals derived from a core by eliminating one hydrogen atom, such as the phenyl and naphthyl radicals.

The use of ligands satisfying the aforesaid formula is advantageous in that it makes it possible to carry out the first stage at ambient temperature so as to form the intermediate product and then prepare a radiopharmaceutical product with a radiochemical purity of at least 95% by means of the reaction of this intermediate product with a second lagand.

By way of example of carbazic dithio acid derivatives able to be used as a nitrogenous lagand, these may be S-methyldithiocarbazate, S-methyl-N-methyldithiocarbazate, alpha-N-methyl-S-methyl beta-N-pyridylmethylene dithiocarbazate, S-methyl-beta-N-( 2-hydroxyphenyl)methylene dithiocarbazate and alpha-N-methyl-S-methyl-beta-N-(2-hydroxyphenyl) methylenedithiocarbazate.

When it is desired to embody the reaction at ambient temperature, it is preferable that the first lagand satisfies the aforesaid formula:

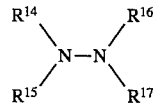

in which $R^{14}$, $R^{15}$ and $R^{16}$ are hydrogen atoms, $R^{17}$ represents the radical with the formula $SO_2R^{18}$ with $R^{18}$ having the significance given above, or the radical with the formula $$-COH, -COCH_2CH_2CONHNH_2 \text{ or}$$

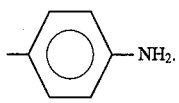

By way of examples, when $R^{14}$, $R^{15}$ and $R^{16}$ are hydrogen atoms and $R^{17}$ represents $SO_2R^{18}$, $R^{18}$ may be the phenyl radical, the p-methylphenyl radical, the 1,3,5-trichlorophenyl radical or the 1,3,5-trimethylphenyl radical.

It is also possible to prepare the radiopharmaceutical products of the invention by means of a second method including the following stages:
1) an oxygenous compound of the transition metal M in a solution is made to react with a) a nitrogenous ligand constituted either by a pharmaceutically acceptable ammonium nitride or metal nitride, or by a nitrogenous compound comprising a pattern >N-N< in which the Ns are linked to hydrogen atoms and/or monovalent organic groups, or in which of the Ns is linked to the carbon atom of a bivalent organic group by means of a double linkage, the other N being linked to hydrogen atoms and/or monovalent organic groups, and b) a reducing agent constituted by either a pharmaceutically acceptable metal or ammonium dithionite, or by tin (II) present in an ionic form in the solution, and 2) making the intermediate product obtained in the first stage to react with a compound satisfying the formula:

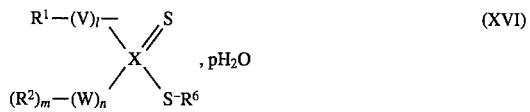

in which $R^1$, $R^2$, V, W, l, m, n and X have the significance given above,
$R^6$ being an alkaline metal ion, $H^+$ or $NH_4^+$, and p being equal to 0 or a whole number from 1 to 5.

In this second method, instead of using phosphines or polyphosphines of the first method, a reducing agent is used constituted by either tin (II) or by a pharmaceutically acceptable metal or ammonium dithionite.

This considerably simplifies establishing new radiopharmaceutical products, such as technetium-based products, as the toxicity and the biological effects of tin like tin chloride are well-known, this not proving to be the case for the phosphines and polyphosphines of the first method.

In fact, tin has been used for a long time for preparing pyrophosphate, methylenediphosphonate and hydroxymethylenediphosphonate type technetium complexes.

Furthermore, the tin compounds (II) and the dithionites are generally soluble in water, which simplifies the preparation of the transition metal nitruro complex since this may be carried out in an aqueous solution, that is in a suitable medium for administering it to man and living creatures.

In this second method, it is possible to carry out two reactions successively or simultaneously.

However, it is preferable to carry out the two reactions successively.

This second method may be implemented in different ways which depend in particular on the reducing agent used and the choice of the nitrogenous ligand and the compound (XII) used in the second stage.

According to a first embodiment of this second method, tin (II) is used as a reducing agent and is introduced into the solution from one or several reactive agents able to keep it in an ionic form in the presence of the nitrogenous ligand and possibly in the presence of the compound (XII) so as to avoid any precipitation of the tin complexes likely to be formed with the nitrogenous ligand or the compound (XII).

Thus, it is possible to introduce the tin in the form of a tin salt (II) when the anion of this tin salt possesses better complexing power on tin than the other reactive agents present in the solution, that is the nitrogenous ligand and possibly the compound (XII).

By way of example, the tin salt may be tin tartrate or oxalate.

It is also possible to introduce the tin (II) and keep it in an ionic form in the solution from other tin salts, especially tin chloride, provided that a complexing agent is simultaneously added to the solution, this agent having a complexing power with respect to the tin of being stronger than that of the nitrogenous ligand and the compound (XII) possibly used in the second stage.

In this case, tin chloride (II) and a suitable complexing agent are added to the solution of the transition metal oxygenous compound and the nitrogenous ligand.

Examples of complexing agents able to be used may be ammonium or alkaline metal pyrophosphates, ammonium or alkaline metal glucoheptonates, ammonium or alkaline metal diethylene triamino pentacetates, ammonium or alkaline metal ethylenediaminotetracetates, ammonium or alkaline metal diamino-1,2 propane N,N,N',N'-tetracetates, ammonium or alkaline metal gluconates, ammonium or alkaline metal methylenediphosphonates, ammonium or alkaline metal hydroxymethylenediphosphonates and ammonium or alkaline metal citrates.

According to a second embodiment of this second method, the reducing agent is a pharmaceutically acceptable metal or ammonium dithionite.

The pharmaceutically acceptable metal dithionites may in particular be the dithionites of alkaline metals, such as sodium dithionite.

As has been seen earlier, the reaction between the oxygenous compound of the transition metal, the nitrogenous ligand and the reducing agent is preferably embodied in an aqueous solution whose pH is adjusted to a suitable value. However, it is also possible to operate with alcoholic or hydroalcoholic solutions.

In order to embody the reaction, a sterile solution of the transition metal oxygenous compound is aseptically introduced, a sterile solution of the nitrogenous ligand and the reducing agent being added to said first sterile solution, the pH of said sterile solution of the reducing agent having been adjusted to the desired value by adding acid, a base or an appropriate buffer. Then the reaction may be effected at ambient temperature or at a higher temperature ranging, for example from 50° to 100° C., for variable periods which depend in particular on the temperature used.

Generally speaking, this operation is carried out with molar oxygenous compound ratios of the transition metal/nitrogenous ligand of $10^{-7}$ to $10^{-2}$.

Following this reaction, it is possible to add the compound of formula (XII) and leave it to react at ambient temperature or a higher temperature of, say, 37° to 45° C. in the case of a monoclonal antibody for variable periods which depend in particular on the temperature used. With conventional ligands, a temperature exceeding ambient temperature may be used and could be from 50° to 100° C.

Generally speaking, this operation may be carried out with molar ratios of the oxygenous compound of the transition metal/compound of formula (XII) of $10^{-7}$ to $10^{-2}$.

In this second stage, it is also possible to adjust the pH of the solution to a suitable value by introducing the compound (XII) into an aqueous solution having a suitably adapted pH.

It is also possible to carry out this second stage in the presence of other additives, such as a complexing agent making it possible to avoid the tin reacting with the compound used (XII) and especially to avoid the formation of precipitates.

As mentioned previously, this second stage is preferably carried out in an aqueous solution but it could also be carried out in an alcoholic or hydroalcoholic solution or even carry out the first and second stages in different solutions, for example having the first stage in an aqueous solution and the second in an alcoholic or hydroalcoholic solution or vice versa.

When the radiopharmaceutical product of the invention is intended to be used for diagnosis, it is generally necessary to prepare it at the time of use.

The invention also concerns a kit for preparing a radiopharmaceutical product with a cardiac tropism and which includes:

a first flask containing a phosphine or a reducing agent selected from pharmaceutically acceptable metal dithionites, ammonium dithionite and tin (II) in an ionic form;

a second flask containing ammonium nitride, the nitride of a pharmaceutically acceptable metal or a nitrogenous ligand, and a third flask containing a compound satisfying the formula:

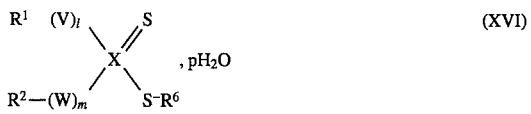

in which $R^1$, $R^2$, V, W, l, m, n and X have the significance given above, $R^6$ being an ion of an alkaline metal, $H^+$ or $NH_4^+$, p being equal to 0 or a whole number of from 1 to 5.

With this kit, it is possible to directly prepare the desired radiopharmaceutical product in a nuclear medecine hospital service by mixing the contents of the first two flasks with a solution of the transition metal oxygenous compound, for example a solution of ammonium or alkaline metal pertechnetate and then add to the product obtained the contents of the third flask.

The products present in the first, second and third flasks respectively may be in a liquid or freeze-dried form.

In certain cases, it is possible to mix the contents of the first two flasks prior to use. In this case, the kit shall solely include one first flask containing a phosphine or the reducing agent mixed with the second reactive agent constituted by the nitride or by dithiocarbazic acid or a derivative of the latter, and a second flask containing the compound of formula (XII) given above.

Given the fact that the products are intended to be administered, for example, intravenously, to living beings, it is essential to use appropriate production and implementation conditions so as to obtain suitably sterile and apyrogenous solutions.

In order to prepare the solutions, it is possible to use sterile apyrogenous water or alcoholic or hydroalcoholic solutions and store the solutions under nitrogen.

In order to prepare freeze-dried compositions, the solutions obtained in the same conditions as mentioned above are freeze-dried in a conventional apparatus.

The radiopharmaceutical products of the invention may be used more particularly for scintiscanning the brain.

In this case, after preparing the technetium nitruro complex, the latter is injected into the patient to be examined and the brain is examined by means of scintigraphy.

So as to inject the product, the quantities of the various reactive agents are such so that they approximately correspond to the stoichiometry of the complexes to be obtained. The final quantity injected depends in particular on the reactive agents used and their toxicity.

Generally speaking, satisfactory results are obtained by using full quantities of reactive agents ranging from 0.05 to 0.40 mg/kg of body weight.

The total dose of the transition metal, for example technetium, is generally within a range of 185 to 740 Mbq (5 to 20 millicuries).

After administering the transition metal nitruro complex, a satisfactory examination may be carried out within a period of between 0.5 and 3 hours, thus obtaining a good contrast, clear images and good detection of lesions.

DETAILED EMBODIMENTS OF EXAMPLES

Other characteristics and advantages of the invention shall appear more readily from a reading of the following illustrative non-restrictive examples.

EXAMPLE 1

Preparation of the Nitruro-bis (Dimethyldithiophosphinato) $^{99m}$ Tc(V) Complex (TcNDMDP)

a) Preparation of the intermediate product.

0.4 ml of a solution containing $2.10^{-2}$ mol/l(2.5 mg/ml) of S-methyldithiocarbazate in ethylic alcohol is introduced into a penicilin type flask followed by 0.2 ml of a solution with $2.10^{-2}$ mol/l (5 mg/ml) of triphenylphosphine in ethylic alcohol and 0.1 ml of hydrochloric acid 1N. Then 0.5 to 1 ml of a solution of sodium pertechnetate (Tc $^{99}$m) is added and the reaction is carried out at 80° C. for 30 minutes or at 100° C. for 15 minutes.

b) Preparation of the final complex.

Added to the contents of the flask obtained in stage a), 1 ml of a buffer solution of 0.5M pH 5.0 of sodium acetate and 0.5 ml of a $6.7.10^{-2}$M solution of sodium dimethyldithiophosphinate in the 0.2M pH 5.0 acetate buffer.

The reaction is carried out for 30 minutes at ambient temperature.

The radiochemical purity of the complex obtained is tested by carrying out a chromotogaphy on a thin silica gel film and a 1:1 mixture of dichloromethane and toluene as a solvent.

The complex obtained has an Rf of 0.53±0.03.

If the radiochemical purity is less than 80%, the complex is purified by means of chromatography on a thin preparatory film. In this case, after development of the solvent, the radioactivity corresponding to the location of migration of the pure product is extracted by ethylic alcohol. The radiochemical purity of the final product after this purification is greater than or equal to 93%.

EXAMPLE 2

Preparation of the Nitruro-bis (Diethyldithiophosphinato)$^{99m}$Tc(V) (TcNDEDP) Complex a) Preparation of the intermediate product.

0.2 ml of a solution containing $7.7.10^{-2}$ mol/l (5.0 mg/ml) of sodium nitride in water is introduced into a penicilin type flask and then 0.2 ml of a solution with $2.10^{-2}$ mol/l (5 mg/ml) of triphenylphosphine in ethylic alcohol and 0.1 ml of hydrochloric acid 1N. Then 0.5 to 1 ml of a solution of sodium pertechnetate (Tc-99m) is added and the reaction is carried out at 80° C. for 30 minutes or at 100° C. for 15 minutes.

b) Preparation of the final product.

Added to the contents of the flask obtained in stage a) is 1 ml of a 0.5M pH 5.0 acetate buffer solution and 0.5 ml of a $6.10^{-2}$ M solution of sodium diethyl dithiophosphinate in the 0.2M pH 5.0 acetate buffer.

The reaction is carried out for 30 minutes at ambient temperature.

The radiochemical purity of the complex obtained is tested by carrying out a chromatogaphy on a thin silica gel film and a 1:1 mixture of dichloromethane and toluene as a solvent.

The complex obtained has an Rf of 0.80±0.03.

The radiochemical purity is greater than or equal to 90%.

EXAMPLE 3

Preparation of the Nitruro(dimethyldithiophosphinato, Diethyldithiophosphinato)$^{99m}$ Tc(V) (TcNMEDP) Complex a) Preparation of the intermediate product.

Introduced into a penicilin type flask are:

0.5 to 3 ml of a sterile solution of sodium pertechnetate (technetium-99m) corresponding to a radioactivity of 18 MBq to 3.7 GBq (0.5 at 100 mCi), 1 ml of a phosphate buffer having a molar concentration of 0.1 to 0.5M and a pH of 7.4 to 8, 0.1 to 0.5 ml of an aqueous solution containing $2.10^{-2}$ mol/l (2.7 mg/ml) of S-methyl, N-methyl dithiocarbazate, and 0.1 to 0.3 ml of an aqueous solution containing $1.8.10^{-3}$ mol/l of dihydrated tin chloride (II) and $5.6.10^{-2}$ mol/l of sodium pyrophosphate.

The reaction is carried out at ambient temperature for 30 minutes.

b) Preparation of the final product.

Added to the contents of the flask obtained in stage a) is 1 ml of a 0.5M pH 5.0 buffer acetate and then 0.5 ml of a $6.7.10^{-2}$M solution of sodium dimethyl dithiophosphinate in the 0.2M pH 5.0 acetate buffer and 0.3 mL of a $6.10^{-2}$N solution of diethytdithiophosphinate in the 0.2M pH 5.0 acetate buffer.

The reaction is carried out for 30 minutes at ambient temperature.

The reaction conditions result in the formation of three products: the nitruro-bis(dimethyldithiophosphinato) $^{99m}$ Tc V, nitruro-b is (diethyldithiophosphinato) $^{99m}$Tc V and nitruro( dimethyldithiophosphinato, diethyldithiophosphinato) $^{99}$m Tc V, the latter being statistically favored. This product is separated by means of chromatography on a thin preparatory silica gel film by using dichloromethane and toluene (1:1) as solvents. The locations of the two symmetrical complexes are marked with the aid of a reference sample and the location of the mixed complex is deduced.

This mixed complex is extracted from the silica gel by washing it with ethylic alcohol. The purity of the final product after purification by thin layer chromatography (CCM) is more than 90%.

EXAMPLE 4

Preparation of the Nitruro-bis (N-(N,N Dimethylamino), N-methyl Dithiocarbamato) $^{99m}$Tc(V) (TcN-NDMMDC) Complex a) Preparation of the intermediate product.

Introduced into a penicilin type flask is 0.2 ml of a solution containing $7.7.10^{-2}$ mol/l (5 mg/ml) of sodium nitride in water, followed by 0.4 ml of a solution containing $1.10^{-2}$ mol/l of tris(2-cyanoethyl)phosphine.

Then 0.5 to 5 ml of a sodium pertechnetate ($^{99m}$Tc) is added and the reaction is carried out at 80° C. for 30 minutes or at 100° C. for 15 minutes.

This operation takes place at a pH of close to 7.

b) Preparation of the final product.

Added to the contents of the flask obtained in stage a) is 0.1 ml of a solution of NaOH 1N and 0.5 ml of a solution of N-(N,N dimethylethylamino), N-methyldithiocarbamate of sodium 0.1M in a 0.2M pH 7.6 phosphate buffer solution.

The reaction is carried out at ambient temperature for 30 minutes. The radiochemical purity of the complex obtained is tested by conducting a thin layer chromatography on silica get and by using a solvent constituted by a mixture of ethanol, chloroform, toluene and 0.1M ammonium acetate in the volume ratios of 6:3:3:1. The Rf of the product is 0.60±0.03. The radiochemical purity is more than or equal to 93%.

EXAMPLE 5

Preparation of the Nitruro-bis (N-N,N Diethylethylamino, N-methyl dithiocarbamato) $^{99m}$Tc(V) Complex The same mode of operation is used as in example 1 for preparing the intermediate product.

For preparation of the final product, the mode of operation of example 4 is used by using a solution of 0.1 mol/l of N-(N,N diethylamino), N-methyl dithiocarbamate of sodium in a 0.2M phosphate buffer solution with a pH of 7.6.

The radiochemical purity of the complex obtained is tested by conducting a thin layer chromatography using a silica gel and a solvent constituted by a mixture of ethanol, chloroform, toluene, and ammonium acetate 0.1M in the volume ratios of 6:3:3:1. The Rf of the product is 0.80±0.02.

The radiochemical purity is greater than or equal to 93%.

EXAMPLE 6

Preparation of the Nitruro-bis(N-methylene Methyl Carboxylate, N-methyl Dithiocarbamato) $^{99m}$ Tc (V) Complex The intermediate product is prepared by following the same mode of operation as in example 3, the final product of the flask being prepared as follows:

Added to the contents of the flask obtained in the stage for preparation of the intermediate product is 0.1 ml of a solution of N-methylene carboxylate, sodium N-methyldithiocarbamate at 0.5 mol/l in water.

The reactional diagram appears below:

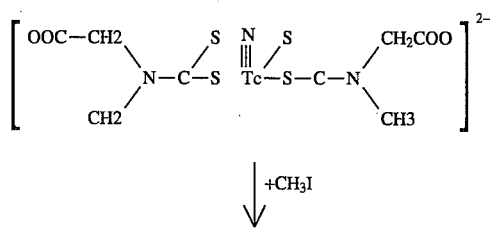

-continued $$\begin{bmatrix} CH_3OOC-CH_2-N-C-S \quad N \quad S-C-N-CH_2CO \\ \phantom{CH_3OOC-CH_2-}CH_3 \phantom{-N-C-}S-Tc-S \phantom{-C-N-}CH_3 \end{bmatrix}^-$$

$$\Big\downarrow +CH_3I$$

$$\begin{bmatrix} CH_3OOC-CH_2-N-C-S \quad N \quad S-C-N-CH_2COOCH_3 \\ \phantom{CH_3OOC-CH_2-}CH_3 \phantom{-N-C-}S-Tc-S \phantom{-C-N-}CH_3 \end{bmatrix}^0$$

The reaction leading to obtaining the nitruro-bis(N-methylene methyl carboxylate, N-methyl dithiocarbamato) $^{99m}$Tc (V) (1) takes place in 10 minutes at ambient temperature.

Added to 0.25 ml of this solution is 1.5 ml of dimethylsulfoxide (DMSO) and 0.2 ml ($3.2,10^{-3}$ mol) of methyl iodide. The esterification reaction of the free carboxyl(s) takes place for 30 minutes at ambient temperature.

The excess quantity of methyl iodide is evaporated under a current of nitrogen and then 1.5 ml of a 0.2M acetate buffer solution, pH 5.0 and 1.5 ml of ethanol are added. The mixture is moved onto a column containing 2 ml of a polystyrene matrix exchanger resin comprising aminoquaternary groups able to fix the compounds having one or several negative charges. Thus, the final product (3), which is neutral, is separated from the original product (1) and the monoester sub-product (2), the latter two products both being charged negatively. The radiochemical purity is tested by chromtography on a thin film of a silica gel by using a solvent constituted by a mixture of ethanol, chloroform, toluene and 0.1M ammonium acetate in the volume ratios of 6:3:3:1. The Rf of the final product is 0.88±0.02. The radiochemical purity is greater than or equal to 95%.

EXAMPLE 7

The biological properties of the complexes obtained in examples 1 to 5 are tested by determining their biodistribution with Sprague Dawley breed male rats weighing 200±20 g.

In this case, the rats, anesthetized with sodium pentobarbital, are injected with a dose corresponding to 15 µmol/kg of the body weight of the complex, which corresponds to a radioactivity dose of from 1 to 2.5 µCi.

5, 30 or 60 minutes after the product has been injected, the rats are killed and organs are removed and the radioactivity present in each organ is determined.

The results obtained are shown on the table I below and expressed in percentages of the injected radioactivity found in the organ following removal and counting.

The values given in each box of the table represent the mean value and the two extreme values.

Also appearing in the table is the ratio between the percentages of the injected radioactivity found per gram of brain and per gram of blood which is an index of the quality of the contrast.

EXAMPLE 8

In this example, the biological properties of the complexes obtained in examples 4 and 6 are tested by determining their recovery in the brain of Macagues Cynomolgus monkeys weighing between 7.5 and 8.5 kg.

The monkeys are anesthetized with ketamine and injected with a dose corresponding to 1.25 µmol/kg of the product described in example 4 and 0.30 µmol/kg of the product described in example 6, which corresponds to a radioactivity dose of between 4 and 6 mCi.

The amount of radioactivity picked up in the brain and the surrounding organs and tissues (heart, lungs, muscles, thyroid, head) is determined via dynamic acquisition between the injection and the end of the examination with a gamma camera, thus defining zones of interest for each organ.

During acquisition, the animal is positioned lying in a right side posture.

The values are expressed as a pixel activity (surface unit) per minute and per mCi; they are not corrected by the radioactive decay of the radioelement.

The results obtained are given in table 2 appearing below.

It is to be noted there is an improved brain/muscle ratio for the complex of example 4 and extremely good cerebral fixation for the complex of example 6.

The radiochemical products of the invention are thus extremely advantageous as a therapy or diagnostic product for the brain.

EXAMPLE 9

Preparation of the Nitruro-bis(N-methylene Ethyl Carboxylate, N-methyl Dithiocarbamato) $^{99m}$Tc (V) Complex The intermediate product is prepared by following the mode of operation as in example 3 and then the final product is prepared as follows.

Added to the contents of the flask obtained in the stage for preparing the intermediate product is 0.1 ml of a solution of N-methylene carboxylate and sodium N-methyl dithiocarbamate at 0.5 mol/l in water.

The reaction resulting in obtaining the nitruro-bis(N-methylene carboxylate, N-methyl dithiocarbamato)$^{99m}$Tc(V) takes place in 10 minutes at ambient temperature.

Added to 0.25 ml of this solution is 1.5 ml of dimethyl sulfoxide (DMSO) and 0.2 ml ($2.5\times10^{-3}$ mol) of ethyl iodide. The esterification reaction of the free carboxyls occurs in 30 minutes at ambient temperature. The excess ethyl iodide is evaporated under a nitrogen current and then 1.5 ml of a solution of 0.2M–pH=5 acetate-buffer and 1.5 ml of ethanol. The mixture is moved onto a column containing 2 ml of an anion echanger resin. Thus, the final product, which is neutral, is separated from the original product and the monoester sub-product, the latter both being charged negatively.

The radiochemical purity is tested by means of thin layer chromatography on silica gel by using a solvent constituted by a mixture of ethanol, chloroform, toluene and 0.1M ammonium acetate in water in the volume ratios of 6:3:3:1. The Rf of the final product is 0.90±0.02. The radiochemical purity is more than or equal to 80%.

EXAMPLE 10

Preparation of the Nitruro-bis (N-methylene Methyl Carboxylate, N-ethyl Dithiocarbamato) $^{99m}$Tc (V) Complex The intermediate product is prepared by following the same mode of operation as in example 3 and then the final product is prepared as follows.

Added to the contents of the flask obtained in the stage for preparation of the intermediate product is 0.1 ml of a solution of sodium N-methylene carboxylate, N-ethyl dithiocarbamate at 0.5 mol/l in water.

The reaction leading to obtaining the nitruro-bis (N-methylene carboxylate, N-ethyl dithiocarbamato) $^{99m}$Tc (V) complex occurs in 10 minutes at ambient temperature.

Added to 0.25 ml of this solution is 1.5 ml of dimethyl sulfoxide (DMSO) and 0.2 ml ($3.2 \times 10^{-3}$ mol) of methyl iodide. The esterification reaction of the free carboxyls takes place in 30 minutes at ambient temperature. The excess methyl iodide is evaporated under a current of nitrogen and then 1.5 ml of a 0.2M pH=5 acetate buffer solution is added, as well as 1.5 ml of ethanol. The mixture is moved onto a column containing 2 ml of an anion exchanger resin. Thus, the final product, which is neutral, is separated from the original product and the monoester sub-product, the latter two products both being charged negatively.

The radiochemical purity is tested by means of thin layer chromatography on silica gel by using a solvent constituted by a mixture of ethanol, chloroform, toluene and 0.1M of ammonium acetate in water with the volume ratios of 6:3:3:1. The Rf of the final product is 0.90±0.02. The radiochemical purity is greater than or equal to 92%.

EXAMPLE 11

Preparation of the Nitruro-bis (N-methylene Methyl Carboxylate, N-propyl Dithiocarbamato) $^{99m}$Tc (V) Complex The intermediate product is prepared by following the same mode of operation as in example 3 and then the final product is prepared as follows.

Added to the contents of the flask obtained in the stage for preparing the intermediate product is 0.1 ml of a solution of sodium N-methylene carboxylate, N-propyl dithiocarbamate at 0.5 mol/l in water.

The reaction leading to obtaining the nitruro-bis (N-methylene carboxylate, N-propyl dithiocarbamato) $^{99m}$Tc (V) complex occurs in 10 minutes at ambient temperature.

Added to 0.25 ml of this solution is 1.5 ml of dimethyl sulfoxide (DMSO) and 0.2 ml ($3.2 \times 10^{-2}$ mol) of methyl iodide. The esterification reaction of the free carboxyls takes place in 30 minutes at ambient temperature. The excess methyl iodide is evaporated under a nitrogen current and then 1.5 ml of a 0.2M pH 5 solution of acetate buffer and 1.5 ml of ethanol is added. The mixture is moved onto a column containing 2 ml of an anion exchanger resin. Thus, the final product, which is neutral, is separated from the original product and the monoester sub-product, the latter two products both being charged negatively.

The radiochemical purity is tested by means of chromatography on a thin film of silica gel by using a solvent constituted by a mixture of ethanol, chloroform, toluene and 0.1M ammonium acetate in water in the volume ratios of 6:3:3:1. The Rf of the final product is 0.92±0.02. The radiochemical purity is greater than or equal-to 95%.

EXAMPLE 12

Preparation of the Nitruro-bis (N-methylene Ethyl Carboxylate, N-n-propyl Dithiocarbamato) $^{99m}$Tc (V) Complex The intermediate product is prepared by following the same mode of operation as in example 3 and then the final product is prepared as follows.

Added to the contents of the flask obtained in the stage for preparing the intermediate product is 0.1 ml of a solution of sodium N-methylene carboxylate, N-propyl dithiocarbamate at 0.5 mol/l in water.

The reaction resulting in obtaining the nitruro-bis (N-methylene carboxylate, N-propyl dithiocarbamato) $^{99m}$Tc (V) complex takes place in 10 minutes at ambient temperature.

Added to 0.25 ml of this solution is 1.5 ml of dimethyl sulfoxide (DMSO) and 0.2 ml ($2.5 \times 10^{-3}$ mol) of ethyl iodide. The esterification reaction of the free carboxyls takes place in 30 minutes at ambient temperature. The excess ethyl iodide is evaporated under a nitrogen current and then 1.5 ml of a solution of a 0.2M, pH 5 solution of an acetate buffer and 1.5 ml of ethanol. The mixture is moved onto a column containing 2 ml of an anion exchanger resin. Thus, the final product, which is neutral, is separated from the original product and the monoester sub-product, the latter two products being charged negatively.

The radiochemical purity is tested by means of chromatography on a thin film of silica gel by using a solvent constituted by a mixture of ethanol, chloroform, toluene and 0.1M of ammonium acetate in water in the volume ratios of 6:3:3:1. The Rf of the final product is 0.92±0.02. The radiochemical purity is greater than or equal to 95%.

EXAMPLE 13

Preparation of the Nitruro-bis (3-(Methyl carboxylate)piperidino Dithiocarbamato) $^{99m}$Tc (V) Complex The intermediate product is prepared by following the same mode of operation as in example 3 and then the final product is prepared as follows;

Added to the contents of the flask obtained in the stage for preparing the intermediate product is 0.1 ml of a solution of sodium (3-carboxylate) piperidino dithiocarbamate at 0.5 mol/l in water.

The reaction resulting in obtaining the nitruro-bis ((3-carboxylate)piperidino dithiocarbamato) $^{99m}$Tc (V) complex takes place in 10 minutes at ambient temperature.

Added to 0.25 ml of this solution is 1.5 ml of dimethyl sulfoxide (DMSO) and 0.2 ml ($3.2 \times 10^{-3}$ mol) of methyl iodide. The esterification reaction of the free carboxyls takes place in 30 minutes at ambient temperature. The excess methyl iodide is evaporated under a nitrogen current and then 1.5 ml of a 0.2M acetate buffer solution, pH 5, and 1.5 ml of ethanol are added. The mixture is moved onto a column containing 2 ml of an anion exchanger resin. Thus, the final product, which is neutral, is separated from the original product and the monoester sub-product, the latter two products both being charged negatively.

The radiochemical purity is tested by means of chromatography on a thin film of silica gel by using a solvent constituted by a mixture of ethanol, chloroform, toluene and 0.1M ammonium acetate in water in the volume ratios of 6:3:3:1. The Rf of the final product is 0.94±0.02. The radiochemical purity is greater than or equal to 95%.

EXAMPLE 14

Preparation of the Nitruro-bis [N-(Methylene Methyl Carboxylate)] Dithiocarbamato) $^{99m}$Tc (V) Complex The intermediate product is prepared by following the same mode of operation as in example 3 and then the final product is prepared as follows.

Added to the contents of the flask obtained in the stage for preparing the intermediate product is 0.1 ml of a solution of sodium bis (methylene carboxylate) dithiocarbamate at 0.5 mol/l in water.

The reaction leading to obtaining the nitruro-bis (methylene carboxylate) dithiocarbamato) $^{99m}Tc$ (V) complex takes place in 10 minutes at ambient temperature.

Added to 0.25 ml of this solution is 1.5 ml of dimethyl sulfoxide (DMSO) and 0.2 ml ($3.2 \times 10^{-3}$ mol) of methyl iodide. The esterification reaction of the free carboxyls takes place in 30 minutes at ambient temperature. The excess methyl iodide is evaporated under a nitrogen current and then 1.5 ml of a solution of a 0.2M, pH 5,buffer solution and 1.5 ml of ethanol are added. The mixture is passed onto a column containing 2 ml of an anion exchanger resin. Thus, the final product, which is neutral, is separated from the original product and the monoester, diester and triester sub-products, the latter products being charged negatively.

The radiochemical purity is tested by means of chromatography on a thin film of silica gel by using a solvent constituted by a mixture of ethanol, chloroform, toluene and 0.1M ammonium acetate in water in the volume ratios of 6: 3: 3: 1. The Rf of the final product is 0.86±0.02. The radiochemical purity is greater than or equal to 85%.

EXAMPLE 15

Preparation of the Nitruro-bis (N-ethylene-2(Methyl Carboxylate), N-methyl Dithiocarbamato)$^{99m}Tc$ (V) Complex The intermediate product is prepared by following the same mode of operation as in example 3 and then the final product is prepared as follows.

Added to the contents of the flask obtained in the stage for preparing the intermediate product is 0.1 ml of a solution of sodium N-ethylene(2(carboxylate), N-methyl dithiocarbamate at 0.5 mol/l in water.

The reaction leading to obtaining the nitruro-bis (N-ethylene(2-carboxylate), N-methyl dithiocarbamato) $^{99m}Tc$ (V) complex takes place in 10 minutes at ambient temperature.

Added to 0.25 ml of this solution are 1.5 ml of dimethyl sulfoxide (DMSO) and 0.2 ml ($3.2 \times 10^{-3}$ mol) of methyl iodide. The esterification reaction of the free carboxyls takes place in 30 minutes at ambient temperature. The excess methyl iodide is evaporated under a current of nitrogen and then 1.5 ml of a 0.2M , pH 5, acetate buffer solution and 1.5 ml of ethanol are added. The mixture is passed onto a column containing 2 ml of an anion exchanger resin. Thus, the final product, which is neutral, is separated from the original product and the monoester sub-product, both the latter two products being charged negatively.

The radiochemical purity is tested by means of chromatography on a thin film of a silica gel by using a solvent constituted by a mixture of ethanol, chloroform, toluene and 0.1M ammonium acetate in water in the volume ratios of 6:3:3:1. The Rf of the final product. The radiochemical purity is greater than or equal to 95%.

EXAMPLE 16 a) Preparation of the sodium N-methylene methyl carboxylate, N-methyl dithiocarbamate ligand.

The ligand is prepared from the chlorhydrate of the methylic ester of sarcosine according to the following reactional diagram:

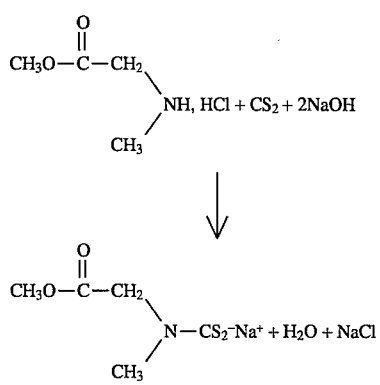

A solution containing 8 g of NaOH (0.2 mols) in 200 ml of methanol is cooled to −10° C. Added to this solution is 14.2 g of sarcosine methyl ester chlorhydrate (0.1 mols) followed by 7.6 g of $CS_2$ (0.1 mols). The above are allowed to react for 30 minutes by keeping the solution at −10° C. The product is then separated on a silica column by using methanol as an eluant. The fractions corresponding to the final product are recombined and the solvent is evaporated. A yellow/brown oil is obtained.

The ligand is characterized by RMN of the proton in the DMSO:

$(CH_3\!-\!O\!-\!\overset{\overset{\displaystyle O}{\|}}{C}\!-\!)$:3.75 ppm - singlet $(\overset{\overset{\displaystyle O}{\|}}{C}\!-\!CH_2\!-\!N\!-\!)$:4.95 ppm - singlet $(CH_3\!-\!N\!-\!)$:3.70 ppm - singlet b) Preparation of the nitruro-bis (N-methylene methyl carboxylate, N-methyl dithiocarbamato) $^{99m}Tc$ complex.

The intermediate product is prepared by following the same mode of operation as in example 3 and then the final product is prepared as follows.

Added to the contents of the flask obtained in the stage for preparing the intermediate product is 3 ml of a solution of sodium N-methylene methyl carboxylate, N-methyl dithiocarbamate at 0.05 mol/l in water. The reaction leading to obtaining the nitruro-bis (N-methylene methyl carboxylate N-methyl dithiocarbamato) $^{99m}Tc$ (V) complex takes place in 10 minutes at ambient temperature.

The radiochemical purity is tested by means of chromatography on a thin film of a silica gel by using a solvent constituted by a mixture of ethanol, chloroform, toluene and 0.1M ammoniuum acetate in water in the volume ratios of 6:3:3:1. The Rf of the final product is 0.88±0.02. The radiochemical purity is greater than or equal to 90%.

Thus, the same complex is obtained as in example 6.

The formulae of the complexes obtained in examples 9 to 16 are given in table 3 following.

EXAMPLE 17

In this example, the properties of the complexes obtained in examples 9 to 16 are tested by determining their recovery in the brain of a monkey according to the same mode of operation as in example 8.

The fixation values are expressed in pulses per pixel, per mCi and per minute and are listed in the table 4 following.

In the light of these results, it shall be observed that the complexes of examples 9, 12 and 14 have an average cerebral fixation and all the other complexes possess good cerebral fixation.

Moreover, the images obtained are of extremely good quality, which demonstrates the advantages of the radio pharmaceutical products of the invention for the optical image formation and therapy of the brain.

TABLE 1

$$\begin{array}{c} CH_3 \\ \diagdown \\ \diagup \\ CH_3 \end{array} PS_2 \quad (VIII) \qquad \begin{array}{c} C_2H_5 \\ \diagdown \\ \diagup \\ C_2H_5 \end{array} PS_2 \quad (IX) \qquad \begin{array}{l} L_1 = (CH_3)_2\,PS_2 \quad (VIII) \\ L_2 = (C_2H_5)_2\,PS_2 \quad (IX) \end{array}$$

| $L_1 = L_2$ | Example 1 | | | Example 2 | | | Example 3 | | | | | |
|---|---|---|---|---|---|---|---|---|---|---|---|---|
| | | | | Time between injection and killing | | | | | | | | |
| Whole organs | 5 min | 30 min | 60 min | 5 min | 30 min | 60 min | 5 min | 30 min | 60 min | 5 min | 30 min | 60 min |
| Liver | 5.7 | 4.8 | 5.2 | 14.7 | 8.9 | 9.4 | 8.0 | 8.1 | 7.5 | | | |
| | 5.2–6.2 | 4.7–5.0 | 5.0–5.3 | 13.8–16.1 | 8.3–9.5 | 8.9–9.7 | 7.9–8.1 | 7.9–8.2 | 7.2–7.8 | | | |
| Kidneys | 2.9 | 3.0 | 3.1 | 8.4 | 8.4 | 7.0 | 5.8 | 5.9 | 7.1 | | | |
| | 2.7–3.0 | 2.8–3.1 | 2.9–3.2 | 7.9–8.6 | 8.0–8.5 | 6.7–7.1 | 5.5–6.0 | 5.7–6.0 | 6.8–7.2 | | | |
| Lungs | 4.7 | 3.7 | 3.3 | 2.3 | 1.7 | 1.1 | 5.5 | 3.8 | 2.8 | | | |
| | 4.5–5.0 | 3.5–3.9 | 3.1–3.5 | 2.1–2.4 | 1.6–1.8 | 0.9–1.2 | 5.4–5.6 | 3.5–4.0 | 2.6–3.1 | | | |
| Brain | 0.81 | 0.57 | 0.65 | 1.26 | 1.12 | 0.74 | 1.35 | 1.26 | 1.86 | | | |
| | 0.78–0.83 | 0.55–0.59 | 0.59–0.67 | 1.20–1.31 | 1.10–1.14 | 0.70–0.76 | 1.25–1.42 | 1.19–1.31 | 1.76–1.92 | | | |
| Heart | 0.88 | 0.74 | 0.86 | 1.06 | 0.83 | 0.53 | 1.13 | 0.94 | 0.90 | | | |
| | 0.85–0.92 | 0.70–0.78 | 0.85–0.91 | 1.02–1.10 | 0.79–0.85 | 0.50–0.55 | 0.98–1.24 | 0.87–0.98 | 0.85–0.95 | | | |
| Total blood | 74 | 65.5 | 59 | 23 | 20.5 | 23 | 50.5 | 45.5 | 39.5 | | | |
| | 70–77.5 | 63.5–68 | 56–62.5 | 21.5–24 | 20–21.5 | 21.5–24 | 46.5–56.5 | 43.5–48 | 38–42 | | | |
| $\dfrac{\text{Brain g}^{-1}}{\text{Blood g}^{-1}}$ | 0.08 | 0.07 | 0.08 | 0.39 | 0.38 | 0.24 | 0.20 | 0.20 | 0.35 | | | |

$$\begin{array}{c} CH_3 \\ \diagdown \\ \diagup \\ CH_3 \end{array}\!\!N\!-\!CH_2\!-\!CH_2\!-\!\underset{\underset{CH_3}{|}}{N}\!-\!CS_2 \quad (IV) \qquad \begin{array}{c} C_2H_5 \\ \diagdown \\ \diagup \\ C_2H_5 \end{array}\!\!N\!-\!CH_2\!-\!CH_2\!-\!\underset{\underset{CH_3}{|}}{N}\!-\!CS_2 \quad (V)$$

| $L_1 = L_2$ | Example 4 | | | Example 5 | | |
|---|---|---|---|---|---|---|
| | Time between injection and killing | | | | | |
| Whole organs | 5 min | 30 min | 60 min | 5 min | 30 min | 60 min |
| Liver | 9.1 | 15.6 | | 9.3 | 17.3 | |
| | 8.7–9.4 | 14.4–16.4 | | 8.7–9.8 | 15.2–18.4 | |
| Kidneys | 7.1 | 6.9 | | 6.7 | 5.4 | |
| | 6.7–7.4 | 6.3–7.6 | | 6.2–7.5 | 5.1–5.7 | |
| Lungs | 28.6 | 11.4 | | 26.9 | 11.8 | |
| | 27.1–29.5 | 10.3–12.7 | | 26.0–27.8 | 11.1–12.5 | |
| Brain | 0.82 | 0.74 | | 0.69 | 0.58 | |
| | 0.78–0.86 | 0.70–0.81 | | 0.67–0.73 | 0.55–0.61 | |
| Heart | 2.1 | 0.70 | | 2.3 | 1.0 | |
| | 1.8–2.3 | 0.61–0.75 | | 2.1–2.5 | 0.95–1.1 | |
| Total blood | 4.4 | 2.0 | | 3.6 | 1.4 | |
| | 4.2–4.8 | 1.8–2.3 | | 3.2–4.1 | 1.3–1.6 | |
| $\dfrac{\text{Brain g}^{-1}}{\text{Blood g}^{-1}}$ | 1.32 | 2.61 | | 1.35 | 2.84 | |

TABLE 2

| Product | Organ | 5 min | 10 min | 30 min | 40 min | 60 min |
|---|---|---|---|---|---|---|
| Complex of ex. 4 | Brain | 2.4 | 6.6 | 10.6 | 8.9 | 10.3 |
| | Muscle | 0.6 | 1.7 | 2.4 | 2.4 | 2.4 |
| $\begin{array}{c} CH_3 \\ \diagdown \\ \diagup \\ CH_3 \end{array}\!\!N\!-\!CH_2CH_2\!-\!\underset{\underset{CH_3}{|}}{N}\!-\!CS_2$ | Brain/muscle | 4.0 | 3.9 | 4.4 | 3.7 | 4.7 |

(V)

TABLE 2-continued
| Product | Organ | 5 min | 10 min | 30 min | 40 min | 60 min |
|---|---|---|---|---|---|---|
| Complex of ex. 6 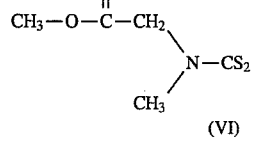 (VI) | Brain | 23 | 39 | 35 | 35 | 33 |
| | Muscle | 4.7 | 15 | 13 | 12 | 12 |
| | Brain/muscle | 4.9 | 2.6 | 2.7 | 2.9 | 2.7 |
TABLE 3
| Examples | Tc complex |
|---|---|
| Ex. 9 | 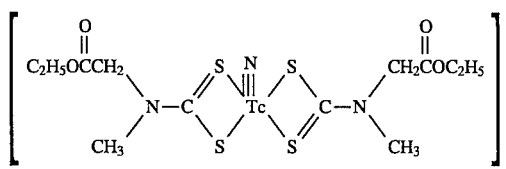 |
| Ex. 10 | 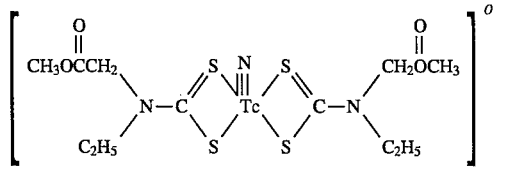 |
| Ex. 11 | 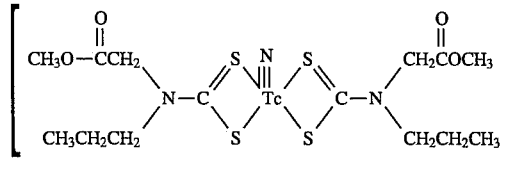 |
| Ex. 12 | 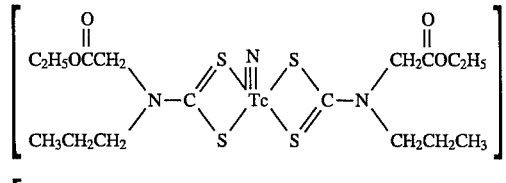 |
| Ex. 13 | 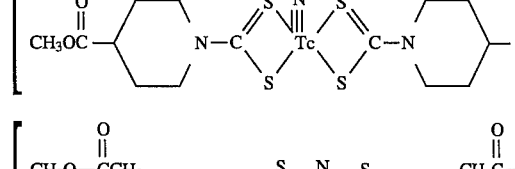 |
| Ex. 14 | 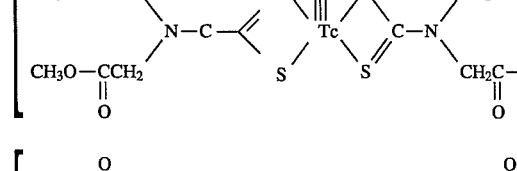 |
| Ex. 15 | 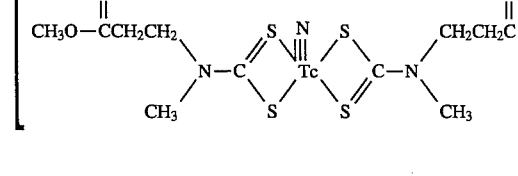 |

TABLE 3-continued

| Examples | Tc complex |
|---|---|
| Ex. 16 | 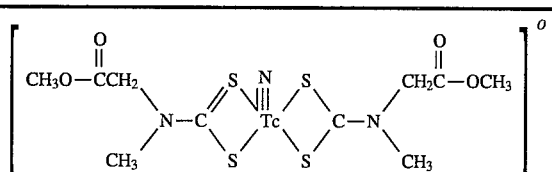 |

TABLE 4

| Product of example | L1 = L2 | | | 5 min | 10 min | 30 min | 40 min | 60 min |
|---|---|---|---|---|---|---|---|---|
| Ex. 9 | C₂H₅OCCH₂—N(CH₃)—CS₂ | | Brain | 25 | 24 | 23 | 21 | 20 |
|  |  |  | Muscle | 9 | 10 | 9 | 8 | 9 |
|  |  |  | Brain/muscle | 2.7 | 2.5 | 2.8 | 2.8 | 2.5 |
| Ex. 10 | CH₃OCCH₂—N(C₂H₅)—CS₂ | | Brain | 52 | 51 | 44 | — | — |
|  |  |  | Muscle | 13 | 14 | 14 | — | — |
|  |  |  | Brain/muscle | 3.9 | 3.7 | 3.4 | — | — |
| Ex. 11 | C₂H₅OCCH₂—N(CH₃CH₂CH₂)—CS₂ | | Brain | 35 | 32 | — | — | — |
|  |  |  | Muscle | 9 | 9 | — | — | — |
|  |  |  | Brain/muscle | 3.9 | 3.6 | — | — | — |
| Ex. 12 | CH₃O—CCH₂—N(CH₃CH₂CH₂)—CS₂ | | Brain | 31 | 29 | 27 | 25 | — |
|  |  |  | Muscle | 12 | 12 | 12 | 11 | — |
|  |  |  | Brain/muscle | 2.6 | 2.4 | 2.4 | 2.4 | — |
| Ex. 13 | CH₃OC-(piperidine)-N—CS₂ | | Brain | 50 | 46 | 37 | 33 | — |
|  |  |  | Muscle | 11 | 10 | 9 | 9 | — |
|  |  |  | Brain/muscle | 4.7 | 4.9 | 4.5 | 4.2 | — |
| Ex. 14 | CH₃O—CCH₂, CH₃O—CCH₂—N—CS₂ | | Brain | 31 | 28 | — | — | — |
|  |  |  | Muscle | 15 | 14 | — | — | — |
|  |  |  | Brain/muscle | 2 | 2.1 | — | — | — |
| Ex. 15 | CH₃O—CCH₂CH₂—N(CH₃)—CS₂ | | Brain | 38 | 34 | 27 | 24 | 20 |
|  |  |  | Muscle | 6 | 5 | 5 | 4 | 3 |
|  |  |  | Brain/muscle | 6.8 | 6.9 | 6.1 | 6.7 | 7.1 |
| Ex. 16 | CH₃O—CCH₂—N(CH₃)—CS₂ | | Brain | 43 | 41 | 38 | 36 | — |
|  |  |  | Muscle | 7 | 8 | 7 | 6 | — |
|  |  |  | Brain/muscle | 5.8 | 5.5 | 5.6 | 6.2 | — |

What is claimed is:

1. A radiopharmaceutical product comprising a complex of a transition metal satisfying the formula:

$$(M\equiv N)L^1L^2 \quad (I)$$

in which M is a radioactive transition metal and in which $L^1$ and $L^2$, which may be identical or different, satisfy the formula:

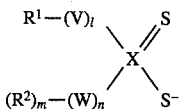

in which $R^1$ and $R^2$, which may be identical or different, represent a linear or branched alkyl radical with 1 to 10 carbon atoms, optionally substituted by at least one group selected from the group consisting of —O—$R^3$, —OOC$R^3$, —COO$R^3$, —CONR$^4$R$^5$ and —NR$^4$R$^5$ in which $R^3$ is a linear or branched alkyl radical with 1 to 5 carbon atoms, and $R^4$ and $R^5$, which may be identical or different, are hydrogen atoms or linear or branched alkyl radicals with 1 to 5 carbon atoms, or in which $R^1$ and $R^2$ together form a bivalent bridging hydrocarbon optionally containing one or several heteroatoms, optionally substituted by at least one group selected from the group consisting of —O—$R^3$, —OOC$R^3$, —COO$R^3$, —CONR$^4$R$^5$ and NR$^4$R$^5$ and —NR$^4$R$^5$ in which $R^3$, $R^4$, $R^5$ are as defined above, V and W, which may be identical or different, represent O, S or Se, X represents C, N—C, P or As, and l, m and n, which may be identical or different, are equal to 0 or 1, m and n being equal to 0 when X represents C, and m being equal to 1 when X represent N—C, P or As, provided, 1) when X represents —N—C—, $R^1$ or $R^2$ is an alkyl radical substituted by at least one group which is a —COOR$^3$ or a —CONR$^4$R$^5$ group, or $R^1$ and $R^2$ together form a —COOR$^3$ or a —CONR$^4$R$^5$ substituted bivalent bridging hydrocarbon optionally containing one or several heteroatoms, and 2) when X represents P, with V and W representing O, $R^1$ and $R^2$ is a —COOR$^3$ or a —CONR$^4$R$^5$ substituted alkyl radical or $R^1$ and $R^2$ together form a —COOR$^3$ or a —CONR$^4$R$^5$ substituted bivalent bridging hydrocarbon optionally containing one or several heteroatoms.

2. Radiopharmaceutical product according to claim 1, wherein at least one of $L^1$ and $L^2$ satisfy the formula:

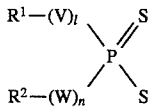

3. Radiopharmaceutical product according to claim 2, wherein l and n are equal to 0.

4. Radiopharmaceutical product according to claim 3, wherein $R^1$ and $R^2$ are methyl or ethyl radicals.

5. Radiopharmaceutical product according to claim 1, wherein

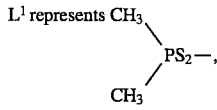

and

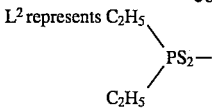

6. Radiopharmaceutical product according to claim 1, wherein at least one of $L^1$ and $L^2$ satisfy the formula:

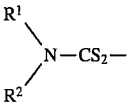

which $R^1$ is an alkyl radical substituted by V-CONR$^4$R$^5$ or —COOR$^3$ and $R^2$ is an alkyl radical optionally substituted by —COOR$^3$.

7. Radiopharmaceutical product according to claim 1, wherein at least one of $L^1$ and $L^2$ satisfies(y) one of the following formulae:

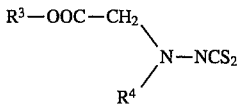

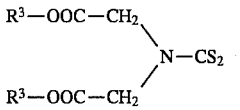

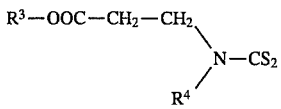

in which $R^3$ is the methyl or ethyl radical and $R^4$ is the methyl, ethyl or propyl radical.

8. Radiopharmaceutical product according to claim 1, wherein $L^1$ and/or $L^2$ satisfy the formula:

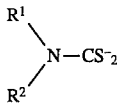

in which $R^1$ and $R^2$ together form bivalent bridging hydrocarbon substituted by a group —COOR$^3$ with $R^3$ representing a linear or branched alkyl radical with 1 to 5 carbon atoms.

9. Radiopharmaceutical product according to any one of claims 1 to 4, wherein $L^1$ and $L^2$ are identical.

10. Radiopharmaceutical product according to claim 1, wherein M represents an isotope of technetium or rhenium.

11. Radiopharmaceutical product according to claim 10, wherein the isotope of the technetium is Tc99m.

12. Radiopharmaceutical product according to claim 10, wherein the isotope of the rhenium is Re-186 or Re-188.

13. Radiopharmaceutical product, wherein it is selected from nitruro-bis (dimethyl)dithiophosphinato) $^{99m}$Tc (V), nitruro-bis (diethyl dithiophosphinato) $^{99m}$Tc (V), nitruro(dimethyldithiophosphinato, diethyldithiophosphinato) TC$^{99m}$(V), nitruro-bis (N-(N,N dimethylethylamino), N-methyl dithiocarbamato) $^{99m}$Tc (V), nitruro-bis (N-(N,N diethylethylamino), N-methyl dithiocarbamato) $^{99m}$Tc (V), nitruro-bis(N-methylenemethylcarboxylate, N-methyl dithiocarbamato )$^{99m}$Tc (V), nitruro-bis (N-methylene ethyl carboxylate, N-methyl dithiocarbamato) $^{99m}$Tc (V), nitruro-bis (N-methylene methyl carboxylate, N-ethyl dithiocarbamato) $^{99m}$Tc (V), nitruro-bis(N-methylene methyl carboxylate, N-propyl dithiocarbamato) $^{99m}$Tc (V), nitruro-bis (N-methylene ethyl carboxylate, N-n-propyl dithiocarbamato) $^{99m}$Tc (V), nitruro-bis (3-(methyl carboxylate)piperidino dithiocarbamato) $^{99m}$Tc (V), nitruro-bis[bis N-(methylene methyl carboxylate]dithiocarbamato)$^{99m}$Tc (V), and nitruro-bis (N-ethylene-2-(methyl carboxylate ), N-methyl dithiocarbamato) $^{99m}$Tc (V).

14. A radio pharmaceutical product according to claim 1, wherein it exhibits a cerebral tropism.

* * * * *

UNITED STATES PATENT AND TRADEMARK OFFICE
CERTIFICATE OF CORRECTION

PATENT NO. : 5,496,929
DATED : March 5, 1996
INVENTOR(S) : Roberto PASQUALINI et al.

It is certified that error appears in the above-indentified patent and that said Letters Patent is hereby corrected as shown below:

On the title page, item [22] and item [87]

should read:

--[22] PCT Filed: Jul. 22, 1992

[87] PCT Pub. No.: WO93/01839

PCT Pub. Date: Feb. 4, 1993--

Signed and Sealed this

Eighteenth Day of June, 1996

*Attest:*

BRUCE LEHMAN

*Attesting Officer*     *Commissioner of Patents and Trademarks*